(12) United States Patent
Nishimura (10) Patent No.: US 11,623,218 B2
(45) Date of Patent: Apr. 11, 2023

(54) FLOW ANALYSIS METHOD, AND FLOW ANALYSIS DEVICE

(71) Applicant: BL TEC K.K., Osaka (JP)

(72) Inventor: Takashi Nishimura, Tokyo (JP)

(73) Assignee: BL TEC K.K., Osaka (JP)

( * ) Notice: Subject to any disclaimer, the term of this patent is extended or adjusted under 35 U.S.C. 154(b) by 0 days.

(21) Appl. No.: 17/791,114

(22) PCT Filed: Jan. 22, 2021

(86) PCT No.: PCT/JP2021/002190
§ 371 (c)(1),
(2) Date: Jul. 6, 2022

(87) PCT Pub. No.: WO2021/153442
PCT Pub. Date: Aug. 5, 2021

(65) Prior Publication Data
US 2023/0035345 A1    Feb. 2, 2023

(30) Foreign Application Priority Data

Jan. 27, 2020   (JP) .............................. JP2020-011231

(51) Int. Cl.
| | | |
|---|---|---|
| *B01L 3/00* | (2006.01) | |
| *G01N 1/44* | (2006.01) | |
| *B01L 5/00* | (2006.01) | |
| *B01L 7/00* | (2006.01) | |
| *G01N 33/18* | (2006.01) | |

(52) U.S. Cl.
CPC ........... *B01L 3/502769* (2013.01); *B01L 5/00* (2013.01); *B01L 7/00* (2013.01); *G01N 1/44* (2013.01); *G01N 33/18* (2013.01); *B01L 2200/16* (2013.01); *B01L 2300/0663* (2013.01); *B01L 2300/0861* (2013.01); *B01L 2300/18* (2013.01)

(58) Field of Classification Search
CPC ........ B01L 3/502769; B01L 5/00; B01L 7/00; B01L 2200/16; B01L 2300/0663; B01L 2300/0861; B01L 2300/18; G01N 1/44; G01N 33/18
See application file for complete search history.

(56) References Cited

U.S. PATENT DOCUMENTS

| | | |
|---|---|---|
| 3,929,411 A | 12/1975 | Takano et al. |
| 2006/0193747 A1 | 8/2006 | Saito et al. |
| 2010/0061891 A1 | 3/2010 | Saito et al. |
| 2011/0198241 A1 | 8/2011 | Murakami |
| 2015/0251181 A1 | 9/2015 | Saito |

FOREIGN PATENT DOCUMENTS

| | | |
|---|---|---|
| CN | 111103271 | 5/2020 |
| JP | 49-50985 | 5/1974 |
| JP | 10-48221 | 2/1998 |
| JP | 2010-256050 | 11/2010 |
| JP | 2012-150130 | 8/2012 |
| JP | 2015/166707 A | 9/2015 |
| KR | 1559161 B1 | 11/2015 |
| TW | 200612092 | 4/2006 |

OTHER PUBLICATIONS

International Preliminary Report on Patentability, International Application No. PCT/JP2021/002190, dated Jul. 28, 2022, 4 pages.
International Search Report for PCT/JP2021/002190 and its English translation, dated Mar. 30, 2021, 2 pages.
Office Action for TW 110102800, dated Feb. 24, 2022, 4 pages.
Japanese Industrial Standards [Testing methods for industrial wastewater JIS K 0102], 5 pages.
Allowance for KR Patent Application No. 10-2022-7025004, dated Jan. 4, 2023, 3 total pages.

*Primary Examiner* — Christopher Adam Hixson
(74) *Attorney, Agent, or Firm* — Casimir Jones, SC; Robert A. Goetz (57) ABSTRACT

The object of the present invention is to provide a novel flow analysis method and a novel flow analyzer each of which makes it possible to improve accuracy of an analysis. A flow analysis method in accordance with an embodiment of the present invention attains the above object by including: a sample introducing step of introducing a sample into a tube (100); a reagent adding step of adding a reagent to the sample which is transferred through the tube (100); and an analyzing step of quantitatively or qualitatively analyzing the sample to which the reagent has been added and further including, after the reagent adding step and before the analyzing step, a gas-liquid separating step of sequentially removing gas which is present in the tube (100).

5 Claims, 8 Drawing Sheets

FLOW ANALYSIS METHOD, AND FLOW ANALYSIS DEVICE

TECHNICAL FIELD

The present invention relates to a flow analysis method and a flow analyzer.

BACKGROUND ART

In the "Testing methods for industrial wastewater" (see Non-Patent Literature 1 below) of Japanese Industrial Standards, a method in which a reagent such as nitric acid or hydrochloric acid is added to a sample (water sample) and then a heat treatment is carried out is specified as to a pretreatment for an analysis of a metal element contained in the sample. This pretreatment, which is carried out mainly for the purpose of decomposition of an organic matter, a suspended matter, and a metal complex that coexist in a sample, is considerably time-consuming. In addition, the pretreatment requires measures to be taken to prevent a worker from being exposed to acid during the pretreatment.

In these regards, it is desired that, by use of a "flow analysis method" such as a flow injection analysis (abbreviated to "FIA") method or a continuous flow analysis (abbreviated to "CFA") method, the pretreatment is automated and thereby the speed of a treatment of a sample is increased and a working environment is improved.

CITATION LIST

Non-Patent Literature

[Non-patent Literature 1]
Japanese Industrial Standards "Testing methods for industrial wastewater (JIS K 0102)"

SUMMARY OF INVENTION

Technical Problem

By the way, in a case where an acidic reagent or an alkaline reagent is added to a sample containing a metal component, gas may be generated as a result of a reaction between the sample and the reagent. In a case where gas is generated in a tube while the aforementioned flow analysis method is carried out, problems, such as a problem that it becomes difficult to carry out an accurate analysis, arise.

In particular, it is confirmed that, in a case where a solution containing hydrogen peroxide is used as a reagent or in a case where a heat treatment is carried out after a reagent is added, generation of gas and an increase in pressure inside a tube become remarkable.

The present invention has been developed in view of the above technical problems, and the object thereof is to provide a novel flow analysis method and a novel flow analyzer each of which makes it possible to improve accuracy of an analysis.

Solution to Problem

A flow analysis method in accordance with an aspect of the present invention, which solves the above technical problems, is a flow analysis method including: a sample introducing step of introducing a sample into a tube; a reagent adding step of adding a reagent to the sample which is transferred through the tube; and an analyzing step of quantitatively or qualitatively analyzing the sample to which the reagent has been added, the flow analysis method further including, after the reagent adding step and before the analyzing step, a gas-liquid separating step of sequentially removing gas which is present in the tube (hereinafter, referred to as "inventive analysis method").

In a preferable aspect, the inventive analysis method further includes, after the reagent adding step and before the gas-liquid separating step, a heating step of carrying out a heat treatment with respect to the sample.

In a preferable aspect, the inventive analysis method is arranged such that, in the sample introducing step, a plurality of segments which are separated by gas bubbles are produced by carrying out gas bubble segmentation with respect to the sample that is introduced.

In a preferable aspect, the inventive analysis method is arranged such that a solution which contains hydrogen peroxide is used as the reagent that is added in the reagent adding step.

A flow analyzer in accordance with an aspect of the present invention, which solves the above technical problems, is a flow analyzer including: a sampling device that is for introducing a sample into a tube; a reagent adding device that adds a reagent to the sample which is transferred through the tube; and an analyzing device that quantitatively or qualitatively analyzes the sample to which the reagent has been added, the flow analyzer further including a gas-liquid separating device that sequentially removes gas which is present in the tube (hereinafter, referred to as "inventive analyzer").

In a preferable aspect, the inventive analyzer further includes a gas bubble segmenting device that produces, in the tube, a plurality of segments which are separated by gas bubbles, by carrying out gas bubble segmentation with respect to the sample that is introduced into the tube.

In a preferable aspect, the inventive analyzer further includes a heating device that carries out a heat treatment with respect to the sample to which the reagent has been added.

Advantageous Effects of Invention

According to an aspect of the present invention, it is possible to improve accuracy of an analysis.

DESCRIPTION OF EMBODIMENTS

The following will discuss embodiments of the present invention with reference to the drawings. Note, however, that the present invention is not limited to the embodiments.

Embodiment 1

<Inventive Analyzer 1>

Figure 1:
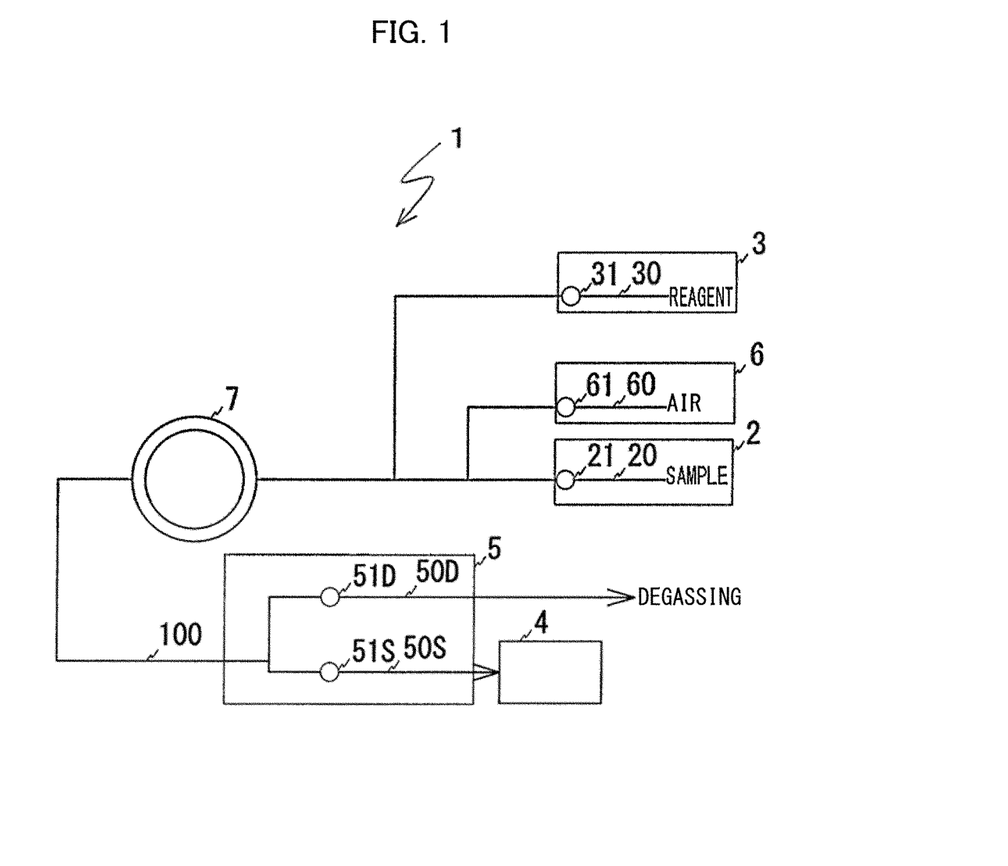
FIG. 1 is a schematic block diagram illustrating an inventive analyzer in accordance with Embodiment 1.

FIG. 1 illustrates an embodiment of an inventive analyzer 1. The inventive analyzer 1 includes a "sampling device 2", a "reagent adding device 3", an "analyzing device 4", and a "gas-liquid separating device 5". The inventive analyzer 1 further includes a "gas bubble segmenting device 6" and a "heating device 7".

—Sampling Device 2—

The sampling device 2 has a role of sampling a sample and introducing the sample into a tube 100. In Embodiment 1, the sampling device 2 is constituted by a thief tube 20 through which the sample is led to the tube 100 and a sampling pump (peristaltic pump) 21 which imparts a suction force to the thief tube 20.

—Reagent Adding Device 3—

The reagent adding device 3 has a role of adding a reagent to the sample which is transferred through the tube 100. In Embodiment 1, the reagent adding device 3 is constituted by a reagent addition tube 30 through which the reagent is introduced into the tube 100 and a reagent addition pump (peristaltic pump) 31 which imparts a suction force to the reagent adding tube 30.

—Analyzing Device 4—

The analyzing device 4 has a role of quantitatively or qualitatively analyzing the sample to which the reagent has been added. In Embodiment 1, an ICP optical emission spectrometer is used as the analyzing device 4.

—Gas-Liquid Separating Device 5—

The gas-liquid separating device 5 has a role of sequentially removing gas which is present in the tube 100. In Embodiment 1, the gas-liquid separating device 5 is constituted by (i) a three-way tube which is provided to a downstream end of the tube 100 and which branches into an analysis tube 50S that extends downward and a degassing tube 50D that extends upward, (ii) an analysis pump (peristaltic pump) 51S which imparts a suction force to the analysis tube 50S, and (iii) a degassing pump (peristaltic pump) 51D which imparts a suction force to the degassing tube 50D.

—Gas Bubble Segmenting Device 6—

The gas bubble segmenting device 6 has a role of carrying out gas bubble segmentation with respect to the sample which has been sampled by the sampling device 2. In Embodiment 1, the gas bubble segmenting device 6 is constituted by an air introduction tube 60 through which air is led to the tube 100 and an air introduction pump (peristaltic pump) 61 which imparts a suction force to the air introduction tube 60.

—Heating Device 7—

The heating device 7 has a role of carrying out a heat treatment with respect to the sample which is transferred through the tube 100. In Embodiment 1, the heating device 7 is constituted by a heater which is provided in the middle of the tube 100.

<Inventive Analysis Method>

The inventive analyzer 1 having the above configuration is a device for carrying out an inventive analysis method. In the inventive analysis method, a "sample introducing step", a "reagent adding step", a "gas-liquid separating step", and an "analyzing step" are carried out. Note that, in Embodiment 1, a "heating step" which is carried out by the heating device 7 included in the inventive analyzer 1 is also carried out after the reagent adding step is carried out and before the gas-liquid separating step is carried out.

—Sample Introducing Step—

Figure 2:
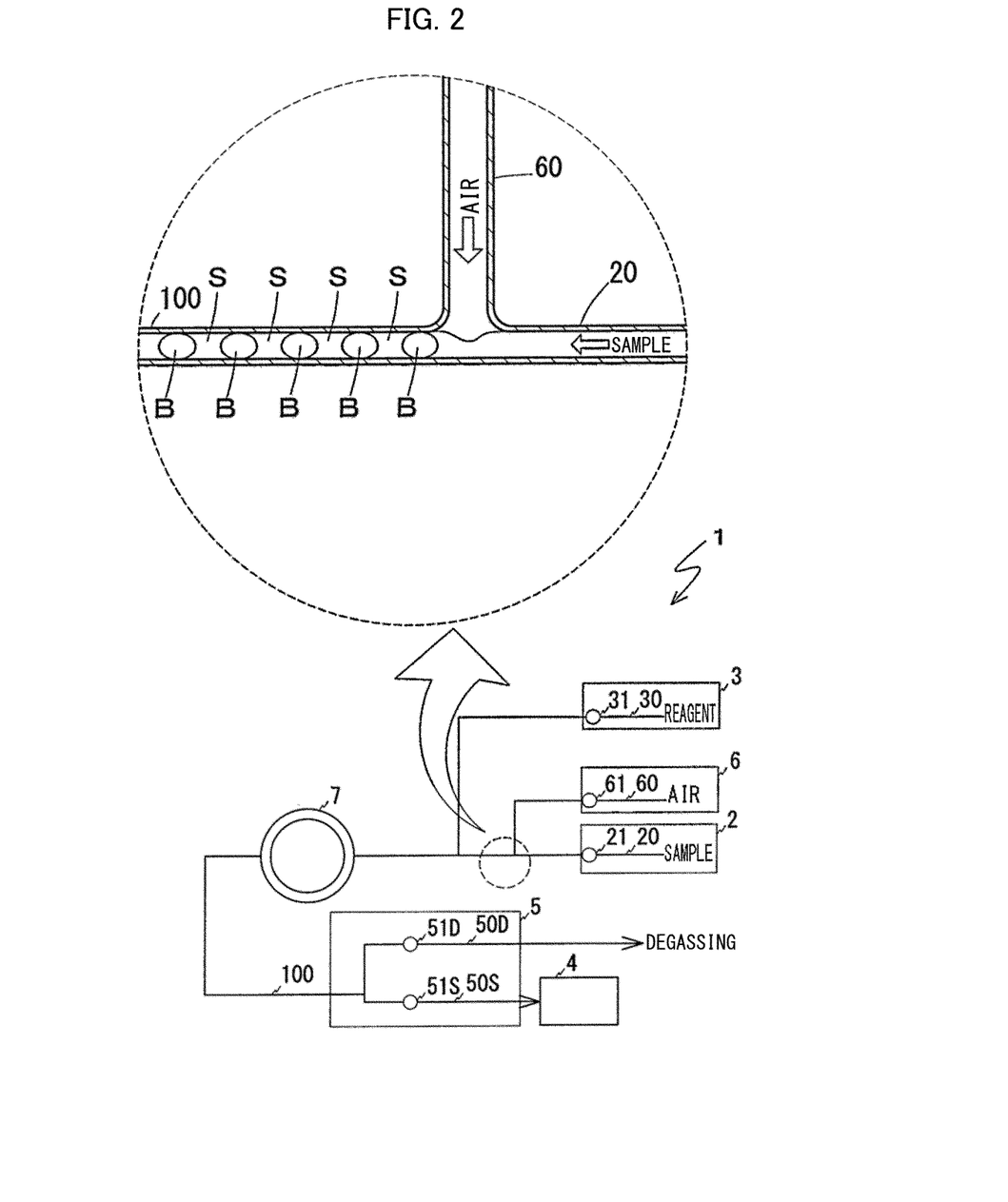
FIG. 2 is a schematic block diagram of the inventive analyzer and a cross-sectional view illustrating, in an enlarged manner, a part which carries out a sample introducing step.

In the sample introducing step, the sample is introduced into the tube 100. As illustrated in FIG. 2, in Embodiment 1, the sample is introduced into the tube 100 with use of the sampling device 2. Note that, in Embodiment 1, a plurality of segments (S) which are separated by gas bubbles (B) are produced by carrying out gas bubble segmentation, in which air is introduced, with use of the gas bubble segmenting device 6 while the sample is introduced into the tube 100.

—Reagent Adding Step—

Figure 3:
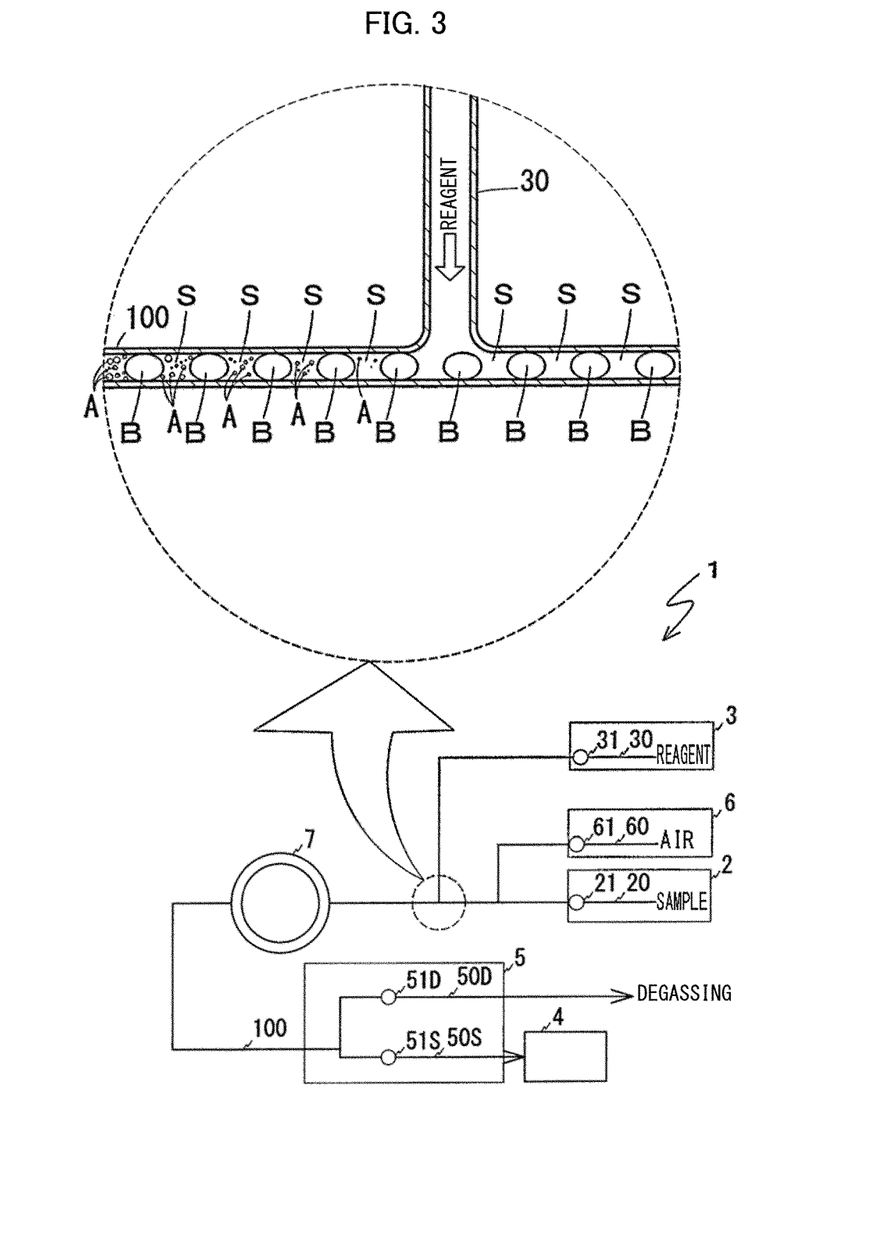
FIG. 3 is a schematic block diagram of the inventive analyzer and a cross-sectional view illustrating, in an enlarged manner, a part which carries out a reagent adding step.

In the reagent adding step, the reagent is added to the sample which is transferred through the tube 100. As illustrated in FIG. 3, in Embodiment 1, the reagent is added to a flow of the sample which is transferred through the tube 100, with use of the reagent adding device 3. By the reagent adding step being carried out, the sample and the reagent contact with each other, and are transferred through the tube 100 while reacting with each other. The reaction between the sample and the reagent may cause generation of gas (A), and the gas (A) thus generated turns into bubbles in the plurality of segments (S).

—Heating Step—

Figure 4:
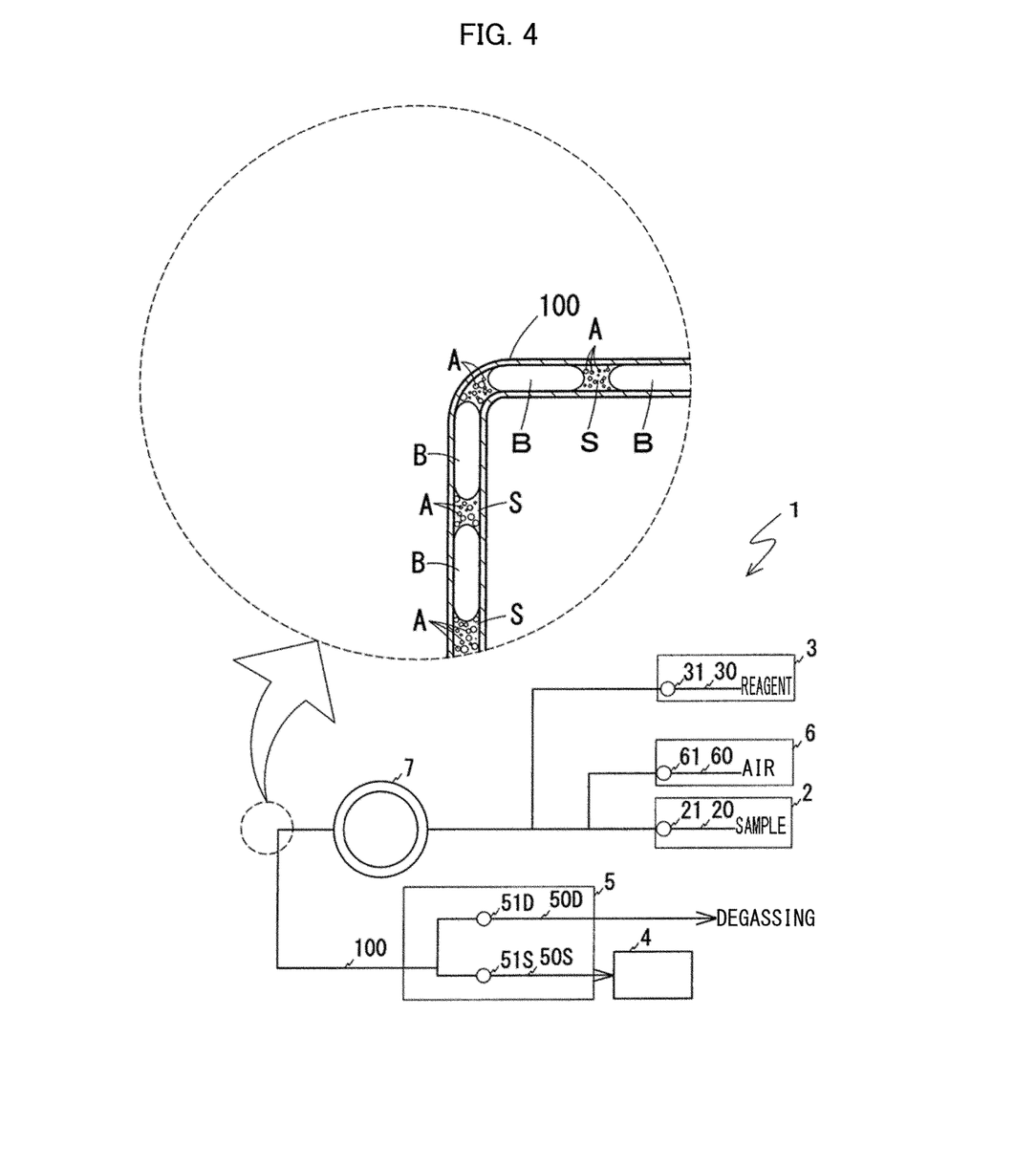
FIG. 4 is a schematic block diagram of the inventive analyzer and a cross-sectional view illustrating, in an enlarged manner, a tube through which a sample which has been subjected to the reagent adding step and a heating step is transferred.

In the heating step, the heat treatment is carried out with respect to the sample which is transferred through the tube 100. In Embodiment 1, the heating step is carried out by heating a part of the tube 100 with use of the heating device 7 and causing the sample to sequentially pass through the heated part of the tube 100. By carrying out the heating step, the reaction between the sample and the reagent is promoted. As illustrated in FIG. 4, the gas (A) which has been generated by the reaction between the sample and the reagent expands while the heating step is carried out. Further, the gas bubbles (B) which have been introduced into the tube 100 together with the sample while the sample introducing step is carried out also expand.

—Gas-Liquid Separating Step—

Figure 5:
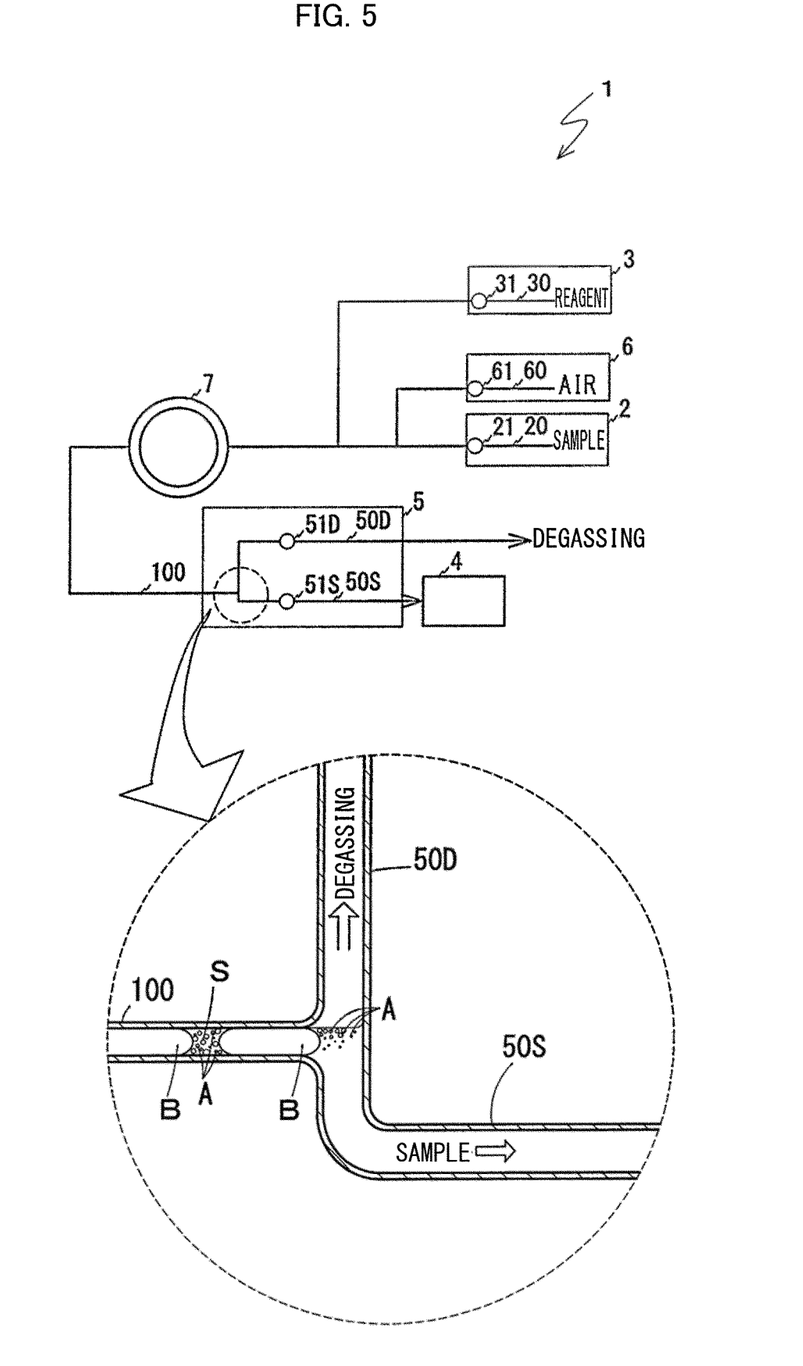
FIG. 5 is a schematic block diagram of the inventive analyzer and a cross-sectional view illustrating, in an enlarged manner, a part which carries out a gas-liquid separating step.

In the gas-liquid separating step, the gas (A) which is present in the tube 100 is sequentially removed. As illustrated in FIG. 5, in Embodiment 1, the gas (A) which is present in the tube 100 is removed with use of the gas-liquid separating device 5. The gas (A) which is present in the tube 100 rises upward, and is therefore removed through the degassing tube 50D which extends upward at the downstream end of the tube 100 (degassing). Note that the gas bubbles (B) which have been introduced into the tube 100 together with the sample are also removed through the degassing tube 50D. The degassing pump 51D which is provided in the middle of the degassing tube 50D has a role of determining the speed of discharge of the gas (A) and the gas bubbles (B).

—Analyzing Step—

In the analyzing step, the sample which has been reacted with the reagent is quantitatively or qualitatively analyzed. As illustrated in FIG. 5, in Embodiment 1, the analyzing step is carried out by introducing the sample from which the gas (S) has been removed into the analyzing device 4 through the analysis tube 50S which extends downward at the downstream end of the tube 100. The analysis pump 51S which is provided in the middle of the analysis tube 50S has a role of determining the speed of introduction of the sample which is introduced into the analyzing device 4 through the analysis tube 50.

In the inventive analysis method in which the aforementioned steps are carried out, the analyzing step is carried out after the gas-liquid separating step of removing the gas (A) and the like which are present in the tube 100 is carried out at the downstream end of the tube 100. Therefore, the gas (A) and the like do not become inhibitors, such as noise, which inhibit measurement, and accordingly it is possible to improve accuracy of an analysis.

By the way, in Embodiment 1, a mechanism is employed such that, while the sample is introduced into the tube 100 in the sample introducing step, the plurality of segments (S) which are separated by the gas bubbles (B) are produced by carrying out the gas bubble segmentation, in which air is introduced, with use of the gas bubble segmenting device 6 (i.e., mechanism pursuant to a continuous flow analysis method). Note, however, that in an embodiment of the present invention, the plurality of segments (S) do not necessarily need to be produced while the sample is introduced into the tube 100. Further, in Embodiment 1, the heating step of carrying out the heat treatment with respect to the sample to which the reagent has been added is carried out. Note, however, that in an embodiment of the present invention, the heating step does not necessarily need to be carried out.

Figure 6:
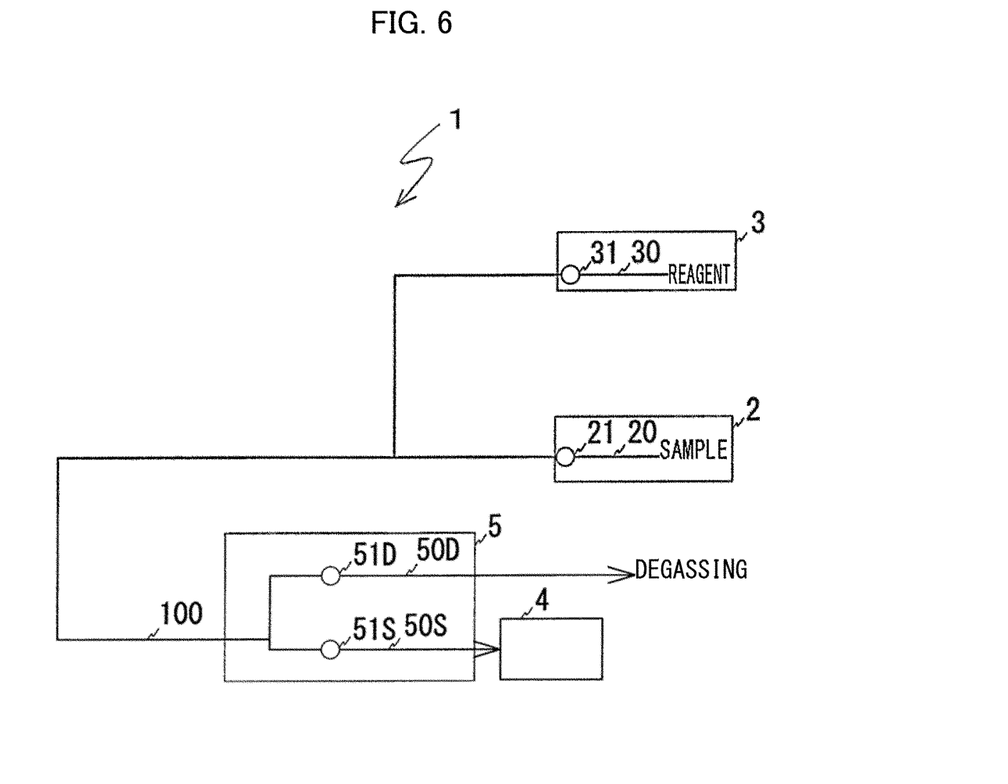
FIG. 6 is a schematic block diagram illustrating another embodiment of the inventive analyzer.

That is, in an embodiment of the present invention, for example, a mechanism may be employed such that the sample is introduced directly into the tube 100 (i.e., mechanism pursuant to a flow injection analysis method) as in another aspect of the inventive analyzer 1 illustrated in FIG. 6. Alternatively, a mechanism may be employed such that the heating step is not carried out.

Note, however, that in a case where the heating step is carried out, the reaction between the sample and the reagent is promoted and thereby an increased amount of the gas (A) is generated. In a case where the mechanism pursuant to the continuous flow analysis method is employed and the heating step is carried out, not only the gas (A) but also the gas bubbles (B) expand. However, in the inventive analysis method in which the gas (A) and the gas bubbles (B) are removed by carrying out the gas-liquid separating step, even in a case where the heating step and the mechanism pursuant to the continuous flow analysis method are employed, the gas (A) and the gas bubbles (B) do not become inhibitors, and the reaction is promoted by the heating step. Further, by carrying out the gas bubble segmentation in the sample introducing step, it is possible to prevent diffusion of the sample in the tube 100.

Therefore, a preferable aspect of the present invention is such that the heating step of carrying out the heat treatment with respect to the sample is carried out. Further, a preferable aspect of the present invention is such that, while the sample introducing step is carried out, the plurality of segments which are separated by the gas bubbles are produced by carrying out the gas bubble segmentation with respect to the sample that is introduced.

Figure 7:
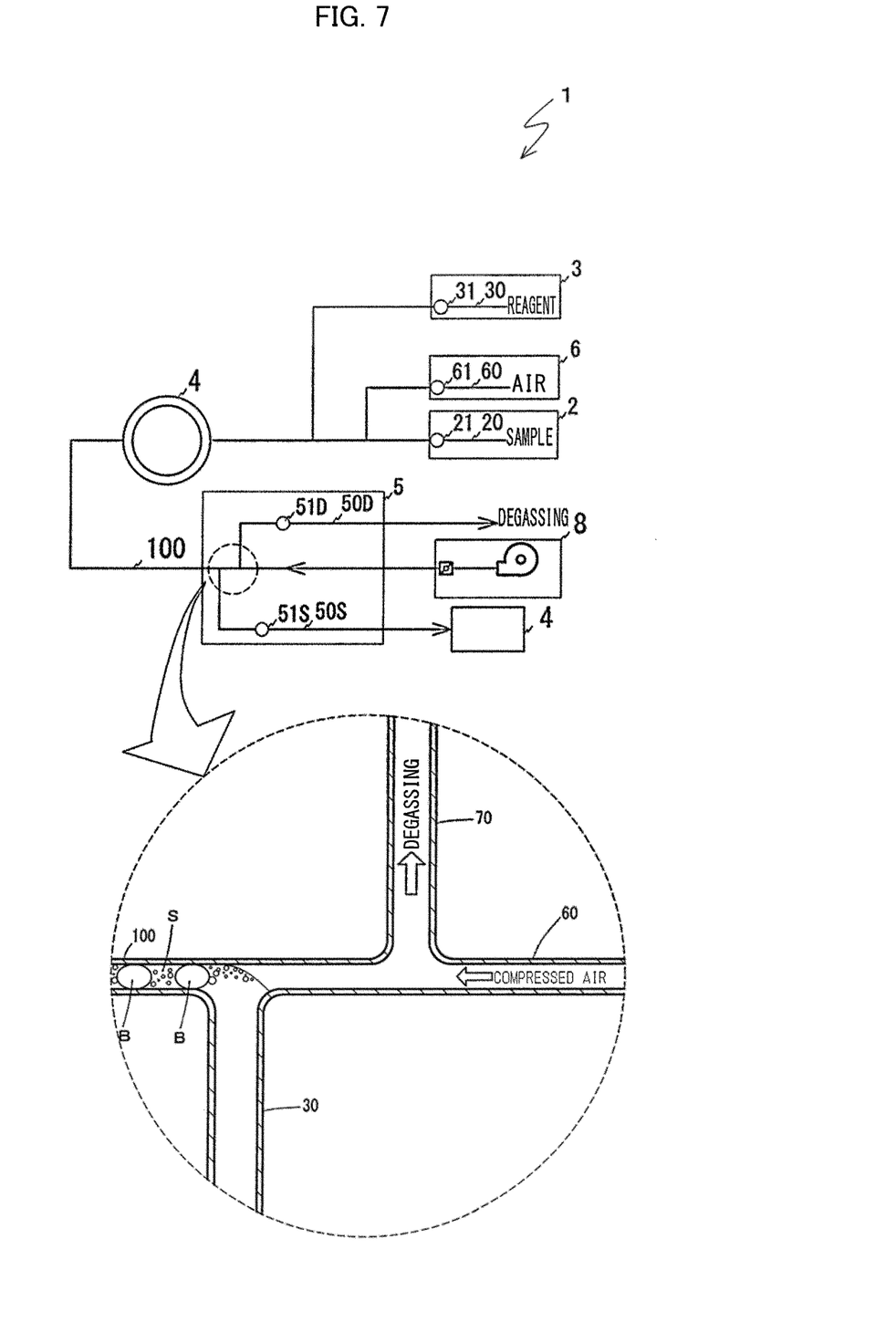
FIG. 7 is a schematic block diagram illustrating, in a partially enlarged manner, further another embodiment of the inventive analyzer.

Note that, in the present invention, in a case where a heating temperature in the heating step is set high or a heating time in the heating step is set long, the gas (A) or the gas bubbles (B) may extremely expand. In such a case, it is confirmed that it is possible to prevent the expansion of the gas (A) and the gas bubbles (B) by carrying out, with use of a pressurizing device 8 which includes a compressor and the like, a pressurizing step of applying pressure against the flow of the sample which is transferred through the tube 100, as illustrated in FIG. 7. Thus, in the inventive analysis method, in a case where the pressurizing step is employed, it is possible to select the heating temperature and the heating time each of which cannot not be employed in the conventional flow analysis method.

In the inventive analysis method, in a case where the pressurizing step is employed, it is possible to set the heating temperature in the heating step to, for example, not lower than 40° C. (more preferably not lower than 90° C.), and it is possible to set the heating time in the heating step to, for example, not shorter than 5 minutes (more preferably not shorter than 30 minutes) per unit of the sample which has been introduced. The pressure applied in the pressurizing step is not limited in particular, and can be determined, as appropriate, depending on the heating temperature and the heating time in the heating step. Preferably, the pressure is set to any pressure of not more than 0.14 MPa (including negative pressure of less than 0.1 MPa, more preferably more than 0.1 MPa and not more than 0.13 MPa).

In Embodiment 1, the ICP optical emission spectrometer is used as the analyzing device 4, which is for carrying out the analyzing step. Note, however, that the analyzing device 4 is not limited to any particular one, and any one of various analyzing devices (for example, flame atomic absorption spectrometer, electrothermal atomic absorption spectrometer, ICP mass spectrometer) can be selected and used as appropriate.

The reagent which is introduced into the tube 100 in the reagent adding step is not limited to any particular one, and is selected as appropriate, depending on necessity of a pretreatment of the sample. Further, a plurality of types of reagents may be added simultaneously or stepwise, if necessary in an analysis. As the reagent, an acidic reagent such as hydrochloric acid, nitric acid, perchloric acid, or sulfuric acid or a basic reagent such as sodium hydroxide or potassium hydroxide can be, for example, selected and used as appropriate. Note, here, that it is confirmed that, in a case where a solution containing hydrogen peroxide is used as the reagent, an increased amount of the gas (A) is generated in the tube 100. In the inventive analysis method in which the gas-liquid separating step is carried out, it is possible to suitably carry out an analysis even in a case where the solution containing hydrogen peroxide is used as the reagent.

Embodiment 2

<Inventive Analyzer 1>

Figure 8:
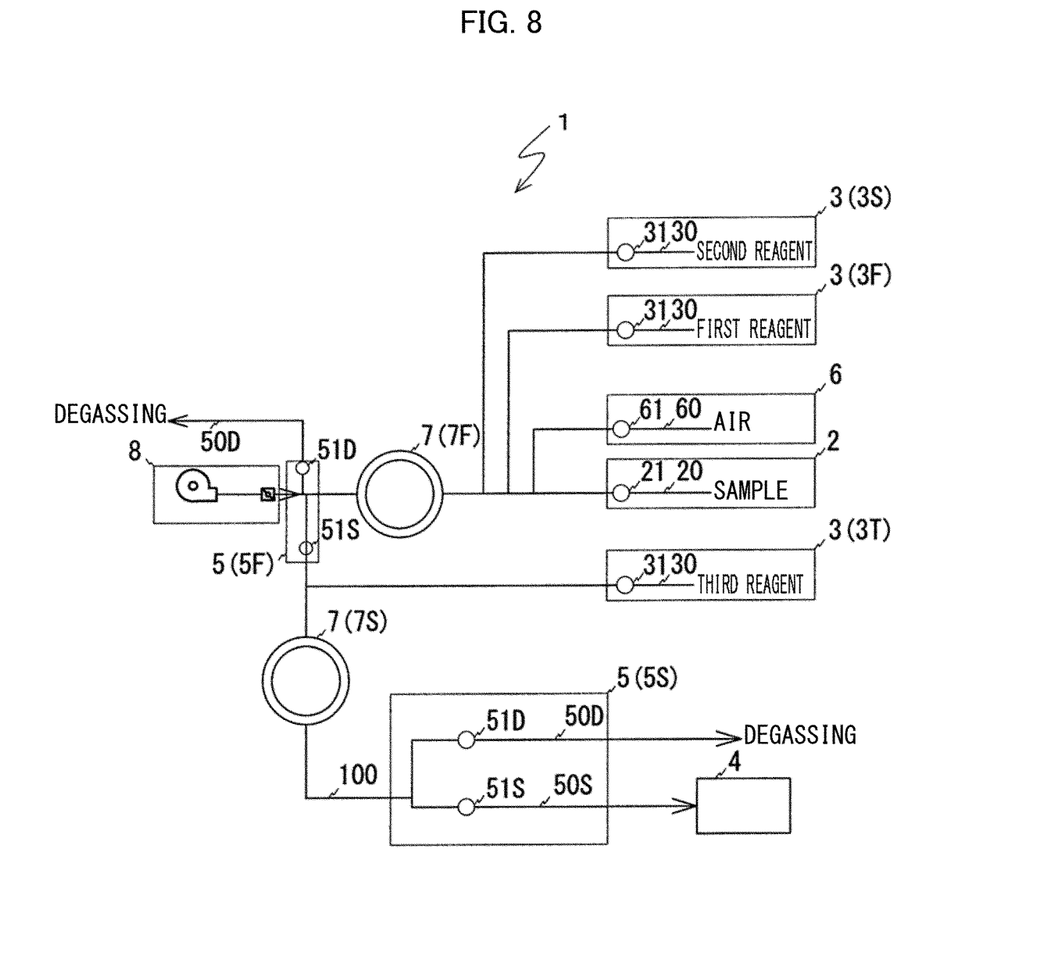
FIG. 8 is a schematic block diagram illustrating an inventive analyzer in accordance with Embodiment 2.

FIG. 8 illustrates an embodiment of an inventive analyzer 1 for carrying out an inventive analysis method. The inventive analyzer 1 includes a "sampling device 2", three "reagent adding devices 3 (3F, 3S, and 3T)", an "analyzing device 4", and two "gas-liquid separating devices 5 (5F and 5S)". The inventive analyzer 1 in accordance with Embodiment 2 further includes a "gas bubble segmenting device 6", two "heating devices 7 (7F and 7S)", and a "pressurizing device 8".

<Inventive Analysis Method>

The inventive analyzer 1 having the above configuration is a device for carrying out the inventive analysis method. In the inventive analysis method, after a "sample introducing step" is carried out, "reagent adding steps (first through third reagent adding steps)" which are carried out in three stages, two "gas-liquid separating steps (first and second gas-liquid separating steps)", and an "analyzing step" are carried out. Furthermore, after the second reagent adding step is carried out and after the third reagent adding step is carried out, "heating steps (first and second heating steps)" are respectively carried out (twice in total).

—Sample Introducing Step—

In the sample introducing step, a sample is introduced into a tube 100. In Embodiment 2, industrial wastewater (water sample) is, for example, used as the sample. Note that, in Embodiment 2, while the sample is introduced into the tube 100, the sample is introduced into the tube 100 with use of the sampling device 2, and gas bubble segmentation, in which air is introduced, is carried out with use of the gas bubble segmenting device 6.

—First Reagent Adding Step—

In the first reagent adding step, a first reagent is added to the sample which is transferred through the tube 100, with use of the reagent adding device 3 (3F). In Embodiment 2, a nitric acid aqueous solution is, for example, used as the first reagent.

—Second Reagent Adding Step—

In the second reagent adding step, a second reagent is added to the sample to which the first reagent has been added, with use of the reagent adding device 3 (3S). In Embodiment 2, a perchloric acid aqueous solution is, for example, used as the second reagent.

—First Heating Step—

In the first heating step, a heat treatment is carried out with respect to the sample to which the first and second reagents have been added, with use of the heating device 7 (7F). By carrying out the first heating step, a reaction between the sample and the first and second reagents is promoted. In a case where a metal component is contained in the sample, gas (for example, hydrogen) is generated in the tube 100 due to the reaction between the sample and the reagents. The gas thus generated (and the air which has been introduced with use of the gas bubble segmenting device 6) attempts to expand by the first heating step being carried out. However, in Embodiment 2, a pressurizing step of applying pressure against a flow of the sample which is transferred through the tube 100 is carried out with use of the pressurizing device 8. Therefore, the expansion of the gas is prevented.

—First Gas-Liquid Separating Step—

In the first gas-liquid separating step, the gas which is present in the tube 100 is removed with use of the gas-liquid separating device 5 (5F).

—Third Reagent Adding Step—

In the third reagent adding step, a third reagent is added to the sample which has been subjected to the first gas-liquid separating step, with use of the reagent adding device 3 (3T). In Embodiment 2, a hydrogen peroxide aqueous solution is, for example, used as the third reagent.

—Second Heating Step—

In the second heating step, a heat treatment is carried out with respect to the sample to which the third reagent has been added, with use of the heating device 7 (7S). By carrying out the second heating step, a reaction between the sample and the third reagent is promoted, and gas (for example, oxygen) is generated in the tube 100 as a result of, for example, decomposition of hydrogen peroxide.

—Second Gas-Liquid Separating Step—

In the second gas-liquid separating step, the gas which is present in the tube 100 is removed with use of the gas-liquid separating device 5 (5F).

—Analyzing Step—

In the analyzing step, the sample which has been reacted with the first through third reagents is quantitatively or qualitatively analyzed.

The inventive analysis method in which the above steps are carried out is established so that a small amount of metal contained in a water sample is automatically analyzed. In the "Testing methods for industrial wastewater" of Japanese Industrial Standards, a pretreatment for an analysis of a metal element contained in a water sample is specified. However, the pretreatment involves a reaction system in which gas is generated, and therefore an automatic analysis by a conventional flow analysis method is not practically carried out. That is, the inventive analysis method in accordance with Embodiment 2 makes it possible to carry out an automatic analysis of a metal element contained in a water sample.

Note, here, that in a conventional analysis method, operations, such as addition of acid, heating, cooling, and dilution in a measuring flask, in a pretreatment need to be manually carried out by a human. In contrast, in the inventive analysis method, it is possible to automatically carry out the operations in the pretreatment, by employing an automatic analysis by a flow analysis method. As a result, in the inventive analysis method, it is possible to prevent occurrence of a human error, increase the speed of a treatment, and improve the efficiency of operations.

The other matters are similar to those described in Embodiment 1, and therefore descriptions thereof will not be repeated and will be omitted.

Note that a person skilled in the art may implement the present invention in the other specific forms without departing from the spirit and the essential features of the present invention. Therefore, the above embodiments are merely illustrative in all respects, and should not be interpreted restrictively. The scope of the present invention is indicated by the appended claims rather than by the foregoing description. Moreover, all changes which come within the meaning and the range of equivalency of the claims are intended to be encompassed in the scope of the present invention.

INDUSTRIAL APPLICABILITY

The present invention is suitably used as a novel flow analysis method and as a novel flow analyzer.

REFERENCE SIGNS LIST

1 Inventive analyzer (flow analyzer)
2 Sampling device
3 Reagent adding device
4 Analyzing device
5 Gas-liquid separating device
6 Gas bubble segmenting device
7 Heating device
8 Pressurizing device
100 Tube

The invention claimed is:
1. A flow analysis method comprising:
a sample introducing step of introducing a sample into a tube;
a reagent adding step of adding a reagent to the sample which is transferred through the tube; and
an analyzing step of quantitatively or qualitatively analyzing the sample to which the reagent has been added, said flow analysis method further comprising:
after the reagent adding step and before the analyzing step, a gas-liquid separating step of sequentially removing gas which is present in the tube:
after the reagent adding step and before the gas-liquid separating step, a heating step of carrying out a heat treatment at a heating temperature of not lower than 40° C. with respect to the sample; and
a pressurizing step of applying, to the gas which is present in the tube and which expands in the heating step, pressure against the flow of the sample which is transferred.

2. The flow analysis method as set forth in claim 1, wherein
in the sample introducing step, a plurality of segments which are separated by gas bubbles are produced by carrying out gas bubble segmentation with respect to the sample that is introduced.

3. The flow analysis method as set forth in claim 1, wherein
a solution which contains hydrogen peroxide is used as the reagent that is added in the reagent adding step.

4. A flow analyzer comprising:
a sampling device that is for introducing a sample into a tube;
a reagent adding device that adds a reagent to the sample which is transferred through the tube; and
an analyzing device that quantitatively or qualitatively analyzes the sample to which the reagent has been added,
said flow analyzer further comprising
a gas-liquid separating device that sequentially removes gas which is present in the tube;
a heating device that carries out a heat treatment at a heating temperature of not lower than 40° C. with respect to the sample to which the reagent has been added;
a pressurizing device that applies, to the gas which is present in the tube and which expands due to the heat treatment, pressure against the flow of the sample which is transferred.

5. The flow analyzer as set forth in claim 4, further comprising
a gas bubble segmenting device that produces, in the tube, a plurality of segments which are separated by gas bubbles, by carrying out gas bubble segmentation with respect to the sample that is introduced into the tube.

\* \* \* \* \*